US012036334B2

(12) United States Patent
Ragg

(10) Patent No.: US 12,036,334 B2
(45) Date of Patent: Jul. 16, 2024

(54) COMPOSITIONS AND DEVICES FOR SCLEROTHERAPY USING LIGHT HARDENING GLUES

(71) Applicant: SWISS VX VENENTHERAPIE UND FORSCHUNG GMBH, Schindellegi Gem Feusisberg (CH)

(72) Inventor: Johann Christof Ragg, Berlin (DE)

(73) Assignee: Swiss VX Venentherapie und Forschung GmbH, Schindellegi Gem Feusisberg (CH)

( * ) Notice: Subject to any disclaimer, the term of this patent is extended or adjusted under 35 U.S.C. 154(b) by 0 days.

(21) Appl. No.: 15/129,080

(22) PCT Filed: Mar. 27, 2015

(86) PCT No.: PCT/EP2015/056760
§ 371 (c)(1),
(2) Date: Sep. 26, 2016

(87) PCT Pub. No.: WO2015/144898
PCT Pub. Date: Oct. 1, 2015

(65) Prior Publication Data
US 2018/0169294 A1 Jun. 21, 2018

(30) Foreign Application Priority Data

Mar. 28, 2014 (EP) .................................. 14162466
Apr. 11, 2014 (EP) .................................. 14164393

(51) Int. Cl.
*A61L 24/00* (2006.01)
*A61L 17/00* (2006.01)
*A61M 25/00* (2006.01)

(52) U.S. Cl.
CPC ......... *A61L 24/0015* (2013.01); *A61L 17/005* (2013.01); *A61L 24/001* (2013.01); *A61L 24/0036* (2013.01); *A61M 25/0084* (2013.01)

(58) Field of Classification Search
CPC ..... A61L 24/00; A61L 24/001; A61L 24/0031
See application file for complete search history.

(56) References Cited

U.S. PATENT DOCUMENTS

| | | | |
|---|---|---|---|
| 5,948,427 A | 9/1999 | Yamamoto et al. | |
| 2004/0215172 A1* | 10/2004 | Chu | A61M 5/00 604/890.1 |
| 2005/0107738 A1* | 5/2005 | Slater | A61M 25/10 604/96.01 |
| 2005/0113798 A1* | 5/2005 | Slater | A61M 25/10 606/213 |
| 2008/0275432 A1* | 11/2008 | Castro | A61K 41/0042 514/777 |
| 2010/0121252 A1* | 5/2010 | Keltner | A61N 5/062 604/20 |
| 2010/0217306 A1* | 8/2010 | Raabe | A61B 17/00491 606/201 |
| 2012/0109191 A1* | 5/2012 | Marano, Jr. | A61B 17/00491 606/213 |
| 2013/0072907 A1* | 3/2013 | Lichty, II | A61B 17/12 604/528 |

FOREIGN PATENT DOCUMENTS

| | | | | |
|---|---|---|---|---|
| EP | 2265896 A1 * | 12/2010 | | G01C 11/02 |
| EP | 2656869 A1 * | 10/2013 | | A61M 25/007 |
| WO | WO-2008/086376 A2 | 7/2008 | | |
| WO | WO-2010/096717 A1 | 8/2010 | | |
| WO | WO-2015/144898 A2 | 10/2015 | | |

OTHER PUBLICATIONS

Material Data Safety Sheet: Ethyl Acryalte (Year: 2008).*
Lewitus et al (Acta Biomaterialia, vol. 7, 2011, pp. 2483-2491 (Year: 2011).*
Nakayama et al (Photocurable Surgical Tissue Adhesive Glues Composed of Photoreactive Gelatin and Poly(ethylene glycol) Diacrylate, Department of Bioengineering, National Cardiovascular Center Research Institute, 1998) (Year: 1998).*
Hamei-Desnos, et al. Evaluation of the efficacy of polidocanol in the form of foam compared with liquid form in sclerotherapy of the greater saphenous vein: initial results Dermatol. Surg. (2003) 29(12): 1170-1175.
Mandley D.J., et al.: "Photon Activated Biological Adhesives in Surgery" International Journal of Adhesion and Adhesives, (2000); 20: 97-102.
Maurins, et al., Distribution and prevalence of reflux in the superficial and deep venous system in the general population—results from the Bonn Vein Study, Journal of Vascular Surgery, (2008) 48(3):680-687.
Yamaki, et al., Comparative study of duplex-guided foam sclerotherapy and duplex-guided liquid sclerotherapy for the treatment of superficial venous insufficiency, Dermatol. Surg. (2004)30 (5): 718-22.

(Continued)

*Primary Examiner* — Micah Paul Young
(74) *Attorney, Agent, or Firm* — BALLARD SPAHR LLP

(57) ABSTRACT

The present invention relates to new compositions for sclerotherapy. In particular, the invention relates to the use of light activated biocompatible glues and catheter for the application of said glue. The catheter of the present invention comprises a light source for the glue activation.

8 Claims, 7 Drawing Sheets

(56) References Cited

OTHER PUBLICATIONS

Figure 1:
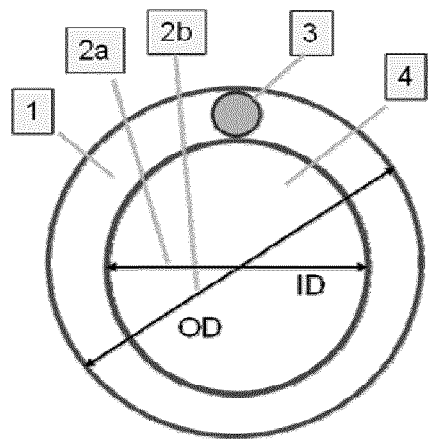
Figure 1:
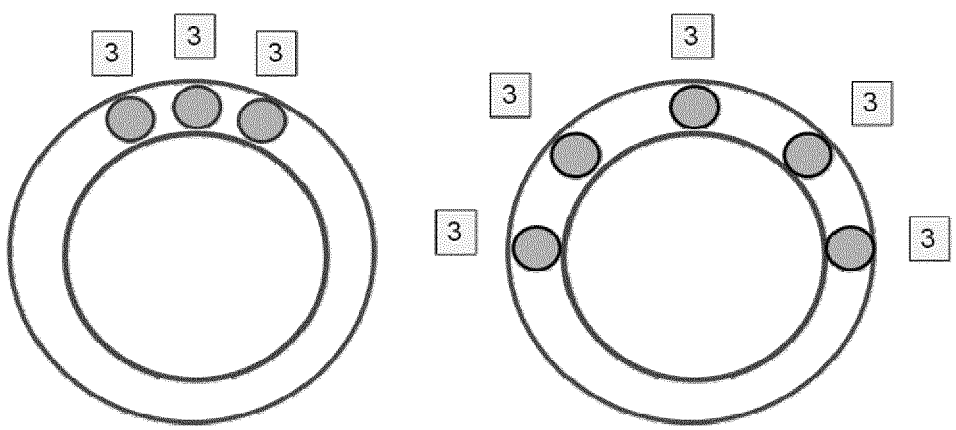
Figure 1:
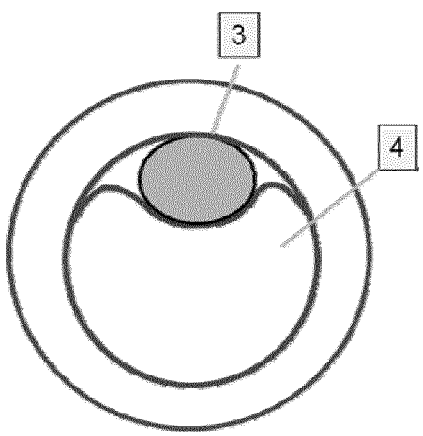
Figure 1:
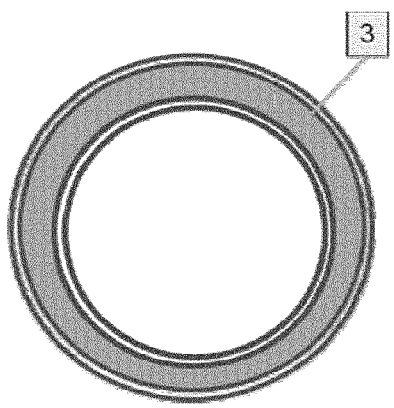
Figure 1:
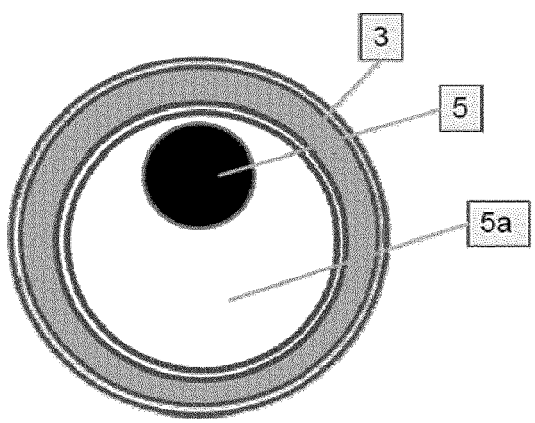

International Search Report and Written Opinion were dated Apr. 13, 2017 by the International Searching Authority for International Application No. PCT/EP2015/056760, which was filed on Mar. 27, 2015 and published as WO 2015/144898 on Oct. 1, 2015 (Applicant-Swiss VX Venentherapie und Forschung GmbH) (13 pages).
International Preliminary Report on Patentability was dated Apr. 18, 2017 by the International Searching Authority for International Application No. PCT/EP2015/056760, which was filed on Mar. 27, 2015 and published as WO 2015/144898 on Oct. 1, 2015 (Applicant-Swiss VX Venentherapie und Forschung GmbH) (8 pages).
International Search Report was dated Dec. 11, 2015 for Application No. PCT/EP2015/056760 which was filed on Mar. 27, 2015 ( Johann Christof Ragg; Applicant-Swiss VX Venentherapie Und Forschung GMBH) (6 pages).
Written Opinion was dated Dec. 11, 2015 for Application No. PCT/EP2015/056760 which was filed on Mar. 27, 2015 ( Johann Christof Ragg; Applicant-Swiss VX Venentherapie Und Forschung GMBH) (6 pages).

* cited by examiner

COMPOSITIONS AND DEVICES FOR SCLEROTHERAPY USING LIGHT HARDENING GLUES

CROSS REFERENCE TO RELATED APPLICATIONS

This application is a national phase filing of International Patent Application No. PCT/EP2015/056760, filed Mar. 27, 2015, which claims priority to European Application No. 14162466.8 filed Mar. 28, 2014, and to European Application No. 14164393.2, filed Apr. 11, 2014, both of which are herein incorporated by reference in their entireties.

FIELD OF THE INVENTION

The present invention is in the field of medicine, more in particular in the field of vein diseases such as venous insufficiency, varicose veins, ectasias or aneurysms in humans and animals. The invention is also in the field of pharmaceuticals and medical devices for treating such diseases.

BACKGROUND

Blood vessels in humans and animals are grouped as arterial and venous, determined by whether the blood in it is flowing away from (arterial) or toward (venous) the heart. Veins collect blood from organs, muscle, connective tissue and skin. Venous blood has a low content of oxygen and nutrients, but enriched in carbon dioxide and other components, such as waste products.

Caused by acquired functional weakness due to lack of activity or by congenital defects, a large number of people show venous congestion in the legs. Congestion means a presence of blood above the physiological level. If no change in habits occurs, congestion turns into insufficiency within few years. Insufficiency means that vein valves become incompetent, resulting in a reversed blood flow. In a vicious circle insufficiency further increases venous blood congestion, and the disease increases with time.

Varicose veins develop from insufficiency. They are superficial veins which have been stressed by an overload of blood for years and therefore show large diameters and a tortuous course. Incompetent leg veins are found in 21-25% of people aged 35 or above, and spider veins even in 50% (Maurins et al. Distribution and prevalence of reflux in the superficial and deep venous system in the general population—results from the Bonn Vein Study, Germany. Journal of Vascular Surgery, Vol 48, Issue 3, September 2008, 680-687).

Beside the cosmetic issues, insufficient and varicose veins lead to major complications, due to the congestion and the poor circulation through the affected limb. The complications comprise pain, heaviness, inability to walk or stand for long hours, skin inflammation, skin damage predisposing skin loss or skin ulcers especially near the ankle, usually referred to as venous ulcers, severe bleeding from minor trauma, blood clotting within affected veins (thrombophlebitis, thrombosis, embolic events).

For dilated veins, surgical removal of the target structure, e.g. varicose veins, has been a widely used therapy for decades. However, like all surgical treatments this may be accompanied by several, partially serious adverse effects, i.e. damaging of adjacent arteries, nerves or lymphatic vessels, generation of wounds and cicatrices, wound infections, or intolerance of the patient for narcotic drugs. Furthermore, the tissue damage going along with every surgery, in particular in junction regions like the groin or the poplitea seems to induce the growth of new, but diseased veins.

As an alternative to surgical removal, different ways of endovenous closure methods have been developed. The term endovenous means, therapy is performed by access through the venous system, and within the diseased vein. The aim of these methods is the permanent closure of the treated vein or vein segment. The effect may be obtained by thermal treatment (e.g. by laser, radiofrequency, steam), or by injection of chemical agents (fluids, foams). Due to the use of catheters and probes, thermal treatment is restricted to relatively linear vessels while chemical agents may also reach curved and tortuous segments, or branched (reticular) veins.

For many applications, today's catheter technique is not yet satisfactory. For example, techniques requiring saline rinsing do not offer particular rinsing catheters. Instead, physicians have to use haemostatic sheaths built for arterial access. Another example are techniques profiting from the absence of blood in the veins to treat, like sclerotherapy, 810-1500 nm endovenous lasers, steam or radiofrequency. For these methods, no particular techniques to achieve absence of blood have been presented so far. Even for meanwhile wide spread foam sclerotherapy no particular foam delivering catheter is commercially available. Significantly, by using simple tube-like catheters, incidental foam misplacements are frequent, and success rates cannot compete with those of thermo-occlusive techniques.

Few other treatment modalities have been reported, relating to other types of venous disease, like varicose veins of the esophagus which are a consequence of liver disease caused vein congestion, with the complication of dangerous bleedings. These bleedings are life-threatening. Emergency examinations are performed by endoscopy (large steerable tubes with fiber optic), and working channels of these endoscopes have been used to inject sclerotic agents or glues. The indication is to stop the bleeding, not the treatment of an insufficiency. These modalities are not endovascular and cannot be applied on peripheral veins.

The use of medical glues in peripheral veins via simple tube like catheters has been evaluated by the inventor since 2007. However, the distribution of glue within the vein was irregular with parts of the endothelium spared from glue because of the high viscosity of the glue. The higher the viscosity of the glue, the worse is the distribution within the vein. Parts with accumulation of too much glue are causing inflammatory reactions. In particular, when using viscous glue with very slow hardening, following the idea to maintain flexibility of the glue, the denaturation of endothelium was incomplete. Also acrylic glues with low viscosity failed in intravenous application, because due to their property of rapid polymerization disturbs a uniform and low-dose distribution along a vein. Furthermore, the application of such glues depends on external manual compression which excludes the use for the most important, but deeper junction regions of the saphenous veins, or perforator veins (veins connecting superficial vessels to the deep venous system). However, if properly feasible, gluing could combine vein closure with immediate diameter reduction.

The effect of all the named endovascular methods applied to peripheral veins is to permanently denature functional proteins in the innermost tissue layer (the endothelial cell layer). Said denaturing process triggers the aggregation of blood cells, in particular thrombocytes, at the vein wall. It is a kind of artificial thrombosis. In contrary to incidental thrombosis which may be hoped to resolve, in the therapeutic approach the aim is to completely denaturize all the endothelium in the segment to treat. Only parts of the vessel wall sufficiently reached by the thermal or sclerotic effect can be expected to close permanently, as undamaged endothelium will revitalize and lead to recurrent pathologic blood flow. Therefore, gluing by use of viscous acrylic glues may initially close a vein but not totally spread to contact all the endothelium and result in recurrence of venous insufficiency.

All endovenous procedures are associated with a local vein spasm, due to effects passing the endothelium layer and reaching the muscular layer. Spasm means a contraction of muscular cells. The vein spasm triggered by endovenous techniques is in general not lasting longer than minutes above the active presence of the modality. However, it would be desirable to maintain the spasm or permanently the vein size reduced by spasm, as one important aim is to decrease the vessel diameter. A real initial shrinking will only be obtained, if the effect reaches deep into the muscular layer with a permanent shortening of fibers. On the other hand, with increasing effects on the muscular layer the danger of vein perforation increases, and so does pain during and after treatment as there are only micrometers distance to the innervated outer wall layer (called adventitia). Therefore, all sclerosant or thermo-occlusive techniques do not initially achieve a sufficient lumen reduction. The vein spasm itself deserves attention, as it is not just an incidental side effect but could be used as a main step for a more effective vein treatment.

Known liquid sclerosant drugs are e.g. alcohols with detergent properties like polidocanol or sodium tetradecylsulphate. In the eldest modality, the liquid sclerosant drug is injected directly into the vessels. Due to its high fluidity the liquid sclerosant drug flows with the blood stream and quickly mixes with blood, soon reaching ineffective dilutions. Protein bindings additionally limit the effect of fluid sclerosant agents.

In order to circumvent some drawbacks of the liquid sclerosant drugs, one usually makes a sclerosant foam by mixing the liquid sclerosant drug with a gas. The resulting sclerosant drug foam is injected into the target structure, e.g. the varicose vein. For foaming the sclerosant drug (e.g. Sodium Tetradecyl Sulfate or polidocanol) is mixed with sterile air or a physiological gas (carbon dioxide) in a syringe or by using mechanical pumps.

Foaming increases the surface area of the drug. Due its higher viscosity, the sclerosant drug foam is more efficient in causing sclerosis than the liquid sclerosant drug (thickening of the vessel wall and sealing off the blood flow; Yamaki et al. (2004) Comparative study of duplex-guided foam sclerotherapy and duplex-guided liquid sclerotherapy for the treatment of superficial venous insufficiency, DermatolSurg 30 (5): 718-22; Hamel-Desnos et al. Evaluation of the Efficacy of Polidocanol in the Form of Foam Compared With Liquid Form in Sclerotherapy of the Greater Saphenous Vein: Initial Results DermatolSurg 29 (12): 1170-1175 (2003)).

All foams, regardless of how they are produced, have several disadvantages: If injected fast enough, foam may replace blood for a certain time, varying from seconds to a few minutes. In this time, the contact to the vein wall is more intense than in case of a liquid bolus just passing by. The chemical reaction of the sclerosant on the endothelium (innermost wall layer) will expand to the media layer and trigger muscular spasms. Therefore, the vein will shrink by spasm to a percentage of 5-80% of its original diameter. The spasm will displace a majority of the foam to neighboring vessels, and at the same time by increased flow resistance prevent the treated segments from relevant perfusion. The vein musculature will relax after 5-60 minutes, and remainders of foam will then be washed away. When the vein spasm vanishes, blood returns to the target vessel. Although by external compression (stockings, bandages) the amount of blood returning to the treated vein can be reduced to some extent, it cannot be completely avoided. The target vein cannot be adjusted to the desired diameter. This is in particular true for deeper veins, in order to compress them effectively one must compress the nearby main veins at the same time, with the consequence of distal congestion. Nevertheless, foam sclerotherapy seems to be an important modality as it is applicable in almost every diseased vein as far as the region is accessible by catheter, and it does not require tumescent or even general anesthesia.

Another way of reducing the amount of blood in a vein during or after endovenous treatments could be to simply lift the leg above heart level. However, this works temporarily and it is not very effective as there is always collateral blood flow due to continuous arterial inflow. A short-term leg elevation will furthermore delay the treatment, increasing the risk of thrombosis. A long-term elevation of the patient's leg (hours to days) would mean immobilization, requiring anticoagulation (e.g. injections of heparin). Some advantages of endovenous treatments, in particular the immediate mobilization and ability for work and sports would be counteracted.

If all the endothelium has been completely denatured, its ability to prevent blood cell adhesion is lost. Therefore, the vein will close within the following 1-24 hours by thrombosis. Some methods are able to achieve immediate thrombosis (e.g. laser 810-980 nm), but they fail in achieving initial lumen reduction, furthermore later-on lumen filling by blood amounts transversing by opened vasa privata, or side branches. With these effects the vein diameter increases, marginal flow may be detected for a few days, but the vein will then close for a longer period, or forever. At this point of terminal vein closure, there is no more perfusion in this vessel, and the pathological backward flow is eliminated. This is the same hemodynamic effect like achieved by surgery ("elimination of reflux"), and it is the main endpoint of treatment quality.

In contrary to surgery, the vein is still in place. For optimal results, it should now be neither visible nor palpable. The patient should not feel its existence when moving or at rest. However, this goal is not achieved with today's techniques.

When, after sclerotherapy or thermo-occlusion of the described kind, blood re-enters the target vein once the spasm is gone, the total amount of clotted blood contained in the vein will determine the duration and symptoms of the reorganization process. Clotted blood within the vessel will have to be removed by metabolization, leading to a change from thrombus to shined connective tissue. As a fact, the incidence of unwanted side effects like painful inflammations, brownish discolorations, long-lasting indurations and visible varicose veins rises with the vein diameter at the time of terminal thrombotic closure.

In clinical practice the majority of sclerotherapies and also thermo-occlusive treatments are not complete in the sense of total circumferential endothelium denaturation. For example, in case of slow injection, and also in case of complex and tortuous varicose formations which limit the injection velocity, foam floats on top of the blood instead of replacing it. Only partial denaturation of the endothelium is achieved. Trials have shown that turning the patient does help. In the case of incomplete endothelium destruction, due to vital endothelium isles painful phlebitis is frequent, and therefore the closure is not stable and shows early relapse.

Hence, sclerosant drug foams of prior art are not well suited for treatment of larger target structures, as they frequently cause painful inflammatory reactions or lack of lasting effects with respect to the occlusion of the target structures.

Other means of non-surgical venous closure, such as radiofrequency, laser or steam (summarized as thermo-occlusive techniques) show this disadvantage in a lesser, but still significant way. They all may achieve a closure of the target vein, but none of them is capable of immediately and sufficiently shrinking the vein. This is in particular true for veins with big diameters (>12 mm). The bigger the vein's diameter, the higher the risk is of leaving vital endothelium isles due to insufficient energy transfer. Besides this, thermo-occlusive techniques require local anaesthesia and cooling fluids which have to be injected in a time consuming manner. Veins with large diameters will, when collapsing, tend to form folds in which endothelium is protected from laser, steam or radiofrequency energy. Furthermore, the effects of these techniques will not include side branches and perforator veins, leaving vital endothelium and therefore incomplete results and sources of relapse.

While thermo-occlusive methods are able to work with a precision of 1-10 mm, sclerotherapies are less precise as fluids or foams will propagate depending on the injected amount, and on the induced spasm which will decrease the lumen and spread the sclerosant towards more or less distant areas. Even very experienced physicians cannot control the effect of sclerosants with a precision less than several centimeters. Side effects are thrombosis (1-3% of the cases), phlebitis (3-18%), occlusion of healthy veins (usually without symptoms and thus greatly underestimated). The lack in precision also leads to frequent failures, thus, sclerotherapy is world-wide said to be a multiple-step treatment. The reimbursement is low.

In the treatment of insufficient veins the method of endovenous gluing has become an alternative. However all technical solutions have drawbacks like using hardly resorbable acrylic adhesives or being not reliable in veins with large diameters. The invention solves these problems by applying a light-activated glue which is preferably biodegradable and/or biocompatible via a newly developed catheter into selected spots within the target vein. Besides light-transferring elements to activate the glue at appropriate times during distribution, the catheter includes means for separating distributed glue from the catheter. In result of the gluing, vein walls are tightly adapted, reducing their diseased diameter for above 75% which is sufficient for best clinical and optical results.

DETAILED DESCRIPTION OF THE INVENTION

The invention relates to a composition for use in treating varicose veins comprising a) a pharmaceutically acceptable tissue glue, b) a sclerosant drug, preferably in the form of a foam, and optionally c) a medical gas, wherein the pharmaceutically acceptable tissue glue is injectable, light-hardening or light-activatable, biodegradable and/or biocompatible, and preferably flexible after hardening.

Foam sclerotherapy is a technique that involves injecting "foamed sclerosant drugs" into a blood vessel using a syringe—here the inventive catheter. The sclerosant drugs (e.g. sodium tetradecyl sulfate or polidocanol) are mixed with air or a physiological gas (e.g. carbon dioxide, oxygen) in a pair of syringes, by using mechanical or electromechanical pumps, or gas pressure. Foaming increases the surface area of the drug. The foam sclerosant drug is more efficacious than the liquid for it mixes less with the blood in the vessel and instead displaces it, thus avoiding dilution of the drug and causing maximal sclerosant action.

Ideally, the glue is in the form of a gel, foam or emulsion.

In a preferred embodiment, the composition comprises 0.001-1.0 g of glue per 100 mm vein segment to be treated, preferably 0.001-0.5 and even more preferably 0.001-0.1 g/100 mm In a more preferred embodiment, the composition comprises 0.01-1.0 g of glue per 100 mm vein segment to be treated, preferably 0.05-0.5 and even more preferably 0.05-0.1 g/100 mm.

The medical gas is selected from the list of carbon dioxide, oxygen, air, or mixtures hereof. In a preferred embodiment the medical gas is carbon dioxide.

The invention further relates to a light-hardening or light-activated glue for use in the treatment of vein diseases.

Preferably the glue is used for treating dilatative or ectatic venous diseases. Hence, the invention also relates to a method of treating a patient which has venous disease.

Preferably, the venous disease is select from the group of venous insufficiency, dilated veins, varicose veins, ectasias or aneurysm.

In a preferred embodiment of the composition according to the invention, glue and gas are loaded in the device and/or applied in subsequent boli.

In contrast to light-hardening or light-activated glues, most of the adhesives developed in medicine are developed for other applications, like cyanoacrylates for skin closure to fibrin-based mixtures for use as lung sealants. Fibrin-based glue either comes from pooled plasma with potential risk of infections (HIV) or is expensive when derived from an autologous source. Common acrylates on the other hand are hardly biodegradable. However, acrylates can be designed to be biocompatible and/or biodegradable. Biodegradable acrylates can also be used for the invention. Such acrylates should have a tissue half-life of less than 2 years Light-activated adhesives are used in technology and also medicine for tasks which require a certain time to bring the objects to a proper position, and then fix them quickly and irreversibly. The adhesive strength is low before activation, and increases with the time of activation unto a certain maximum. For example, ultraviolet-activated glue is used to adhere artificial tooth parts. Even biological adhesives are well known (Photon activated biological adhesives in surgery; Mandley et al., International Journal of Adhesion and Adhesives, Volume 20, Issue 2, 1 Apr. 2000, p. 97-102).

When using an adhesive which is activatable by light or other energies, several steps are mandatory: 1) preparation of the target objects, e.g. removal of interfering particles or fluids, 2) application of the adhesive, 3) supply of a light source near to the adhesive, 4) application of activating light or energy in a way ensuring a separation of adhesive and applying instrument. To fulfill step 4, either the adhesive deposit has to be separated reliably from the deploying instrument, or the activating energy has to be applied in a way NOT activating the glue between the planned deposit and the deploying instrument, i.e. by keeping a particular spatial beam formation. Therefore these steps need to be performed using a catheter.

The invention further relates to a catheter, which comprises a light source to facilitate rapid hardening or activation of the glue. Light source in the context of the present invention encompasses means of generating light at the desired position, e.g. by a LED including conductors for electric power, but also encompasses means to transmit or conduct light to the desired position like glass fiber or polymer fiber. Preferably, the light source is an optical fiber or another light-transmitting element, or the catheter wall is make of a transparent, light-transferring material.

The light generated by the light source may be of any wavelength. Preferably, the light source emits, transmits or conducts UV, visible, or infrared light. In the context of the present invention UV-light is light with a wavelength of between 10 to 380 nm, visible light is light with a wavelength of between 381 to 780 nm and infrared light is s light with a wavelength of between 781 nm to 1 mm.

Preferably the catheter has at least one lumen and an inner diameter of 0.6 to 2.2 mm, an outer diameter of 0.8 to 2.8 mm and a length of 15 to 85 cm. The catheter further comprises a light source, which is preferably a light conducting element integrated within the catheter wall or within one lumen of the catheter.

Sample arrangements for the catheter can be seen in FIGS. 1a-e

In one embodiment of the invention the light source or light conductor is integrated into the catheter wall. In one embodiment the catheter wall comprises a single light source (FIG. 1a). In another embodiment the catheter wall comprises a plurality of light sources (FIG. 1b). The light source may emit or transmit light of different wavelengths or a single wavelength. If a plurality of light sources is present the wavelength of each light source may be selected independently of the others.

In a particular embodiment of the invention a plurality of light sources are used and the light sources are independent from each other.

In an alternative embodiment the light source is integrated in the catheter lumen. In a further embodiment the light source protrudes into the catheter lumen (FIG. 1c, 1e).

In another alternative embodiment the light source comprises a major part of the catheter wall or in a preferred embodiment the catheter wall is the light source (FIG. 1d-e).

In a preferred embodiment the catheter comprises a tube-like container for glue. In a more preferred embodiment the container is light opaque.

In a preferred embodiment the catheter additionally comprises a separation system to prevent glue from sticking to the catheter.

In a preferred embodiment the catheter comprises a relocatable tube for glue deployment: The tube is advanced to a position 0.5-20 mm in front of the main catheter and the intended amount of glue is deployed in this position. Then, the relocatable tube is withdrawn to a position within the main catheter. The light for glue activation is directed towards the glue deposit in a way avoiding exposure of the glue containing tube within the main catheter. Means for light focus may be optical like lenses, or particular geometries of LED or glass fiber tip forms.

Figure 2B:
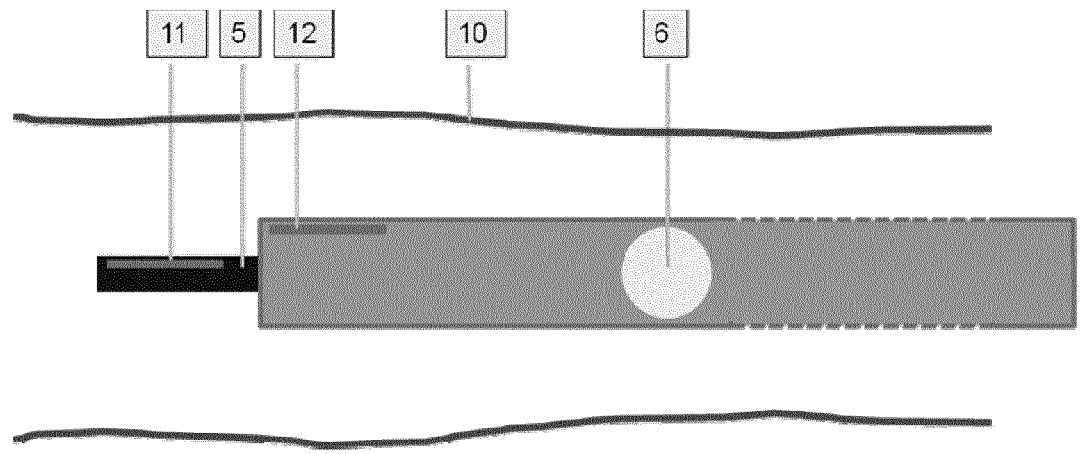
Figure 3A:
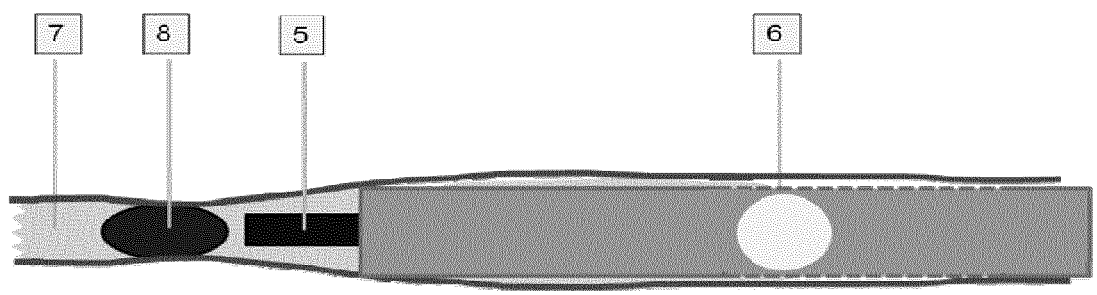

In another embodiment the catheter comprises a fixed tube for glue deployment. In a preferred embodiment of the invention the catheter allows the retraction of the glue column. In one embodiment the fixed tube exceeds the main tube of the catheter (FIG. 3a,b,c). In another embodiment the fixed tube does not exceed the main tube of the catheter In one embodiment the catheter further comprises a sensor system to monitor the quantity of injected glue and/or the function of the separation means by indicating pressure, flow, tube contents, vein contents or contents color. In a preferred embodiment the sensor system comprises a pressure sensor and/or a flow sensor (FIG. 2b).

In a preferred embodiment, the injection catheter is a double-tube catheter

In a further preferred embodiment, glue and gas are loaded into the injection catheter device according to the invention, and applied in subsequent boli. Preferably, the glue is a pharmaceutically acceptable tissue glue. Preferably the glue is also a light-hardening or light-activated glue and the gas is a medical gas acceptable for intravenous use.

In one particular embodiment the catheter is a double-tube injection catheter device comprising:
  a. One larger and one smaller tube, forming a functional unit with the smaller tube positioned within the larger tube,
  b. both tubes are optionally relocatable and demountable,
  c. both tubes have an aperture at both ends,
  d. one aperture being provided in the wall of the outer tube located at a distance of about between 5 mm and 40 mm from the tip, or several apertures positioned in a segment of 5-250 mm from the tip, wherein the diameter of the single aperture is between 70% and 120% of the inner diameter of the outer tube, or in case of several apertures, for each aperture 30-60% of the inner diameter of the outer tube; in case of several apertures: size, shape and distribution are provided in a way providing uniform deployment of a (foam) sclerosant,
  e. a light source or a light conductor
  f. wherein the outer diameter of the inner tube is between 0.6 mm and 2.0 mm, and the inner diameter 0.3-1.6 mm, more preferably 0.4-1.0 mm and even more preferably 0.5-0.8 mm.
  g. the outer diameter of the outer tube is between 1.3 mm and 3.3 mm, and the inner diameter 1.1-3.0 mm, preferably 1.1-2.8 mm and even more preferably 1.1-2.7 mm, a distance between the outer wall of the inner tube and the inner wall of the outer tube is between 0.1 mm to 3.0 mm, preferably 0.1 to 2.5 mm and even more preferably 0.1-2.0 mm.

In specific embodiments, the catheter has one or more of the following dimensions:
  Outer tube's outer diameter: 1.3-2.8 mm, preferably 1.5-2.6 mm, more preferably 1.7-2.4 mm.
  Outer tube's inner diameter: 1.0-2.4 mm, preferably 1.4-2.0 mm, more preferably 1.2-1.8 mm.
  Outer tube's wall diameter/thickness: 0.1-1.5 mm, 0.1-0.3 mm, preferably 0.125-0.25 mm, more preferably 0.15-0.2 mm.

The distance between tip hole and side hole(s) may be 1-50×, preferably 2-50×, preferably 5-40×, even more preferably 15-25× of the outer tube's inner diameter.

The light generated by the light source may be of any wavelength. Preferably, the light source emits, transmits or conducts UV-visible or infrared light.

In one embodiment of the invention the light source is integrated into the catheter wall. In one embodiment the catheter wall comprises a single light source. In another embodiment the catheter wall comprises a plurality of light sources. The light source may emit or transmit light of different wavelengths or a single wavelength. If a plurality of light sources is present the wavelength of each light source may be selected independently of the others.

In a particular embodiment of the invention a plurality of light sources is used and the light sources are independent from each other.

In an alternative embodiment the light source is integrated in the catheter lumen. In a further embodiment the light source protrudes into the catheter lumen.

In another alternative embodiment the light source comprises a major part of the catheter wall or in a preferred embodiment the catheter wall is the light source.

Ideally both tubes are visible in ultrasound imaging, or in another embodiment also in fluoroscopy, phlebography, CT or MRI.

In some embodiments the tip zone of the outer tube is modified such that a flow resistance occurs at the tip. A flow resistance may be achieved by narrowing the inner diameter of the outer tube towards the tip. The outer diameter may remain unchanged or decrease as well at the tip zone resulting in a tapered outer tube. If a tapered outer tube is used, the catheter device may be conveniently introduced into the vein with a lesser risk of damaging the vessel. A flow resistance at the tip zone increases the flow through the side hole(s). This is recommended for application of sclerosant agents, in particular sclerosant foams. Most applications of the present invention make a 100% flow of the foam through the side hole(s) desirable. Preferably, the outflow area formed by the outer tube's tapered tip is smaller than the outflow area formed by the side hole(s).

The catheter dimensions and in particular the side holes are of major importance. All formerly manufactured so called aspiration catheters aim at the collection of thrombus in arteries or veins. Some are merely tubes with a relatively thin wall and hence offer a large lumen. Other catheters provide side holes of small dimensions for the purpose of distributing contrast agent (angiography), or lytic agents (thrombolysis). The present invention is particularly designed for use in veins. Veins are vessels with a very thin and soft wall. The vessels are often tortuous. A vein catheter has to follow the vascular bends, therefore it has to be rather flexible. At the same time, the catheter must provide a certain pushability or stiffness, to reach all the target area. It is favourable if the catheter can be advanced in a vein even without guiding wire.

The side holes have to be relatively large, for two purposes: Large holes allow simple evacuation, end even more importantly, large holes allow the application of foam sclerosants without destroying the foam bubbles, while small holes do. "Large" may be defined by at least 20 times the average foam bubble diameter, preferably larger than 50 times the average foam bubble diameter.

Catheters with one large single side hole are suitable when dealing with short segments, Catheters with more side holes will perform better to treat longer vein segments, as the distribution of the sclerosant medium will be more homogenous. When applying negative pressure on a multi-side hole catheter, in the evacuated regions the vein wall will close the side hole(s) like a valve, focusing the negative pressure on the area being subject to gluing.

To reach the aim of uniform and precise foam sclerosant deployment, the side hole design was adapted to the foam viscosity. For a certain foam for example the side hole size at a position of 10 cm distal to the tip may start with a diameter of 50% relative to the catheters inner lumen, and continue towards the tip with 11 further side holes with diameters reduced stepwise for +2.5%.

The use of a catheter of this kind will provide a very uniform and precise application of foam sclerosant, with a so far unknown quality. However, without additional gluing, it would not fix the vessel to the aimed size.

The position of the catheter/catheters can only be monitored by vision or palpation in very superficial veins (skin level). Under ultrasonography monitoring even tortuous vessels can be followed. If ultrasound imaging should be limited (obesity, scars, gas echoes), a monitoring of catheters can be performed by fluoroscopy or phlebography. If an imaging method using x-ray contrast media is chosen, these media can be applied via the inner or the outer catheter, depending on the desired amount and the degree of blood replacement.

The outer catheter allows administration of contrast media while functional probes (catheter for gluing, laser- or radiofrequency probes, steam or sclerotherapy catheters) are in place. Large amounts of contrast medium can be picked up by use of the aspiration function of the outer catheter which is in particular an advantage in patients with sensitivities against contrast media.

In patients with intolerance or increased risks of contrast media, fluid contrast media usually containing iodine can be replaced by carbon dioxide. Also carbon dioxide may be picked up by aspiration or by opening the outlet via the outer catheter.

In a particular embodiment, the outer tube consists of two relocatable layers or tubes, adding an additional tube of 0.1-0.6 mm wall thickness to the outer tube, spaced apart at 0.1-0.5 mm. The task of the additional tube is to cover or uncover the wall apertures of the outer catheter by sliding it back and forth. In one embodiment, it has a proximal grip, or handle, for easier relocation. In another embodiment, there are proximal markings, on the tubes, or signal device on or within the tube, to indicate the covering status of the outer catheters wall apertures. In a further embodiment, the aperture covering tube has a tapered tip. Its maximal length is defined by the length of the outer catheter minus the length of the side hole area.

The modality using an additional tube to cover or uncover some or all side holes of the outer tube gives the option to use the same catheter for several purposes, like treating straight diseased vessels and single side branch or perforator lesions in the same catheter intervention using one single access. It further more gives the unique option to change from side hole absorption to front hole absorption by covering the side holes.

Preferably, the length of the inner and the outer tube is between 6 cm and 120 cm. The length of the inner tube is always longer than the outer tube, with an exceeding length varying from 0.1-140 cm.

The length is defined by the length of the segment with the maximum length that is to be treated. The distance from the groin to the ankle defines the maximum treatment length, but most of the indications have a much shorter segment.

Ideally, the wall thickness of the outer tube is between 0.1-0.6 mm. Preferably, the wall thickness of the outer tube is 0.1 mm-0.3 mm, more preferably 0.125 mm-0.25 mm, most preferably 0.15 mm-0.2 mm. The wall thickness of the inner tube is ideally between 0.1 mm and 0.4 mm.

It is preferred, that the outer tube has a terminal tip-zone at which the lumen diameter is reduced in total or in parts to provide guidance for the inner tube. Alternatively, the inner tube may have a terminal enlargement with or without increasing the wall thickness, with the purpose of fixation of the inner catheter within the outer catheter, while maintaining the property of easy sliding of the inner tube within the outer tube.

Preferably, the outer tube and/or inner tube are equipped at their ends, with a male or female Luer-lock connector, or another connector type, and/or are connected with an included or separate Y-shaped or T-shaped piece enabling conduction of the inner tube through the entry of the outer tube as well as flushing or evacuation by way of the outer tube, in one embodiment with a grip zone or a handle for easier sliding movements.

The Luer taper is a standardized system of small-scale fluid fittings used for making leak-free connections between a male-taper fitting and its mating female part on medical and laboratory instruments, including hypodermic syringe tips and needles or stopcocks and needles. Named after the 19th century German medical instrument maker Hermann Miffing Luer, it originated as a 6% taper fitting for glass bottle stoppers. Key features of Luer Taper connectors are defined in the ISO 594 standards. It is also defined in the DIN and EN standard 1707:1996 and 20594-1:1993.

Preferably, one, several or all tubes have a tapered tip. It is most preferred that all tubes have a tapered distal terminal tip for easier introduction into the target vein.

Preferably, the inner and/or outer tube is made of or covered with anti-sticking material like polytetrafluoroethylene (PTFE), also known as Teflon or perfluoroalkoxy (PFA). It is preferred that the inner and outer tube is made of or covered with polytetrafluoroethylene (PTFE) also known as Teflon, or PFA, or FEP, or similar plastic material with properties protecting the material from sticking to arbitrary substances. This has been shown to be of great importance as it ensures that the glue and the possibly remaining blood fractions do not stick to the device. Polytetrafluoroethylene (PTFE) is a synthetic fluoropolymer of tetrafluoroethylene that finds numerous applications. The most known brand name of PTFE is Teflon by DuPont Co. PTFE is a fluorocarbon solid, as it is a high-molecular-weight compound consisting wholly of carbon and fluorine. PTFE is hydrophobic: neither water nor water-containing substances wet PTFE, as fluorocarbons demonstrate mitigated London dispersion forces due to the high electronegativity of fluorine.

PTFE has one of the lowest coefficients of friction against any solid body. PTFE is used as a non-stick coating for pans and other cookware. It is very non-reactive, partly because of the strength of carbon-fluorine bonds, and so it is often used in containers and pipework for reactive and corrosive chemicals. It is also used for catheters. Perfluoroalkoxy or PFA is a type of fluoropolymer with properties similar to polytetrafluoroethylene (PTFE). It differs from the PTFE resins in that it is melt-processable using conventional injection molding and screw extrusion techniques. PFA was invented by DuPont and is sold under the brandname Teflon PFA. Teflon is better known as the trade name for PTFE. Other brandnames for granules are Neoflon PFA from Daikin or Hyflon PFA from Solvay Solexis. PFA is very similar in composition to the fluoropolymers PTFE and FEP (fluorinated ethylene-propylene). PFA and FEP both share PTFE's useful properties of low coefficient of friction and non-reactivity, but are more easily formable. PFA is softer than PTFE and melts at 305° C.

It is preferred that the inner and/or outer tube comprise means for fixing the position of the two conduits with respect to each other, such as a broadening, hooks or locks.

It is preferred that the inner and/or outer conduits are combined in the following size configurations (outer diameter):

TABLE 1

| Outer tube | F4 | F5 | F6 | F7 | F8 | F9 | F10 |
|---|---|---|---|---|---|---|---|
| Inner tube | F1-2 | F2-3 | F2-4 | F2-5 | F2-6 | F2-7 | F2-8 |

The French scale or French gauge system is commonly used to measure the size (outside diameter) of a catheter. It is most often abbreviated as Fr, but can often abbreviated as FR or F. It may also be abbreviated as CH or Ch (for Charrière, its inventor) in French speaking countries. 1 Fr=0.33 mm, and therefore the diameter of the catheter in millimeters can be determined by dividing the French size by 3:

$$D(mm)=Fr/3 \text{ or } Fr=D(mm)\times 3$$

For example, if the French size is 9, the diameter is 3 mm.

An increasing French size corresponds to a larger diameter catheter. This is contrary to needle-gauge size, where an increasing gauge corresponds to a smaller diameter catheter. The French gauge was devised by Joseph-Frédéric-Benoît Charrière, a 19th-century Parisian maker of surgical instruments, who defined the "diameter times 3" relationship; See table 2.

TABLE 2

| French (F) | Diameter (mm) | Diameter (inches) |
|---|---|---|
| 3 | 1 | 0.039 |
| 4 | 1.35 | 0.053 |
| 5 | 1.67 | 0.066 |
| 6 | 2 | 0.079 |
| 7 | 2.3 | 0.092 |
| 8 | 2.7 | 0.105 |
| 9 | 3 | 0.118 |
| 10 | 3.3 | 0.131 |
| 11 | 3.7 | 0.144 |

It is preferred if one of the tubes comprises a guide wire (0.14-0.38 inch).

In one embodiment, the tip zone of the inner and/or outer tube is shaped or shapeable for a distance of 1-4 cm to form a curve, covering an angle from 5 to 45 degrees, serving as tool to probe venous curves, junctions, a side branches or perforator veins.

The invention relates to a double-tube injection and aspiration catheter device, wherein the inner tube is replaced, exchanged, replaceable or exchangeable by a metal or metal-like hollow needle with a double- or triple-cut tip.

If choosing a short and small catheter configuration, e.g. outer diameter (OD) F4, length 6-20 cm, a direct introduction to the target vessel can be achieved by adding a hollow needle, fitting in the outer catheter, preferably with double- or triple cut tip.

The double-tube injection may comprise a transparent aspiration chamber.

The invention further relates to a method for sclerotherapy, wherein the treated vein is occluded by glue for less than 20% of its length, preferably less than 15% of its length, more preferably less than 10% of its length and most preferably for less than 5% of its length.

One embodiment of the invention relates to a method for sclerotherapy wherein the vein is occluded using a light-hardening glue. Preferably the glue is deposited in the vein in the form of glue deposits. The glue deposits can have any shape, preferably they are spherical or cylindrical. If the glue deposits are cylindrical, they preferably have a radius of 0.1 to 0.5 mm and a length of 0.1 to 10 mm. The distance between individual glue deposits is preferably between 1*D to 10*D, more preferably 1*D to 5*D, wherein D is the diameter of the vein that is being occluded.

In a preferred embodiment the vein is occluded using light-hardening glue, wherein the glue is disposed in the form of glue dots which are spaced apart at least 2 cm. Preferably the dots are spaced apart 5 cm, more preferably 10 cm. In the most preferred embodiment the dots are spaced apart 5 to 10 cm away from each other.

In a further embodiment, the invention also relates to a kit comprising a composition according to the invention, wherein the glue is a pharmaceutically acceptable and/or biocompatible light-hardening glue, as well as a catheter according to the invention.

EXAMPLE

A laboratory test was performed using a transparent PTFE catheter prototype OD 2.3 mm, ID 1.6 mm of 30 cm length combined with a non-transparent PTFE inner catheter of OD 1.2 mm and ID 0.8 mm, 40 cm in length for glue deployment, both with proximal Luer-adaptors and connected via an Y-connector. In a fresh vein specimen of 20 cm in length and native diameter of 8 mm foam sclerotherapy was performed using injection via the outer catheter, and then 3 spots of 0.05 ml light-activatable acrylic glue were subsequently placed at a distance of 5 cm. UV irradiation was performed after every glue placement by a 8 W UV source transmitting the light through the catheter wall for 20 seconds. The vein sample was taken to histology, where complete endothelium denaturation was shown. All glue spots were firmly adapting the vein walls and proved stable to distracting external forces of 10 N.

FIGURE LEGENDS

FIG. 1a: Catheter for distribution of light-activatable glue, shown as cross-section with catheter wall (1), inner diameter ID (2a), outer diameter OD (2b), light producing or light transmitting elements (3), and catheter lumen (4)

FIG. 1b: The catheter wall may include one or multiple light producing or light transmitting elements (5) in various locations FIG. 1c: The light producing or light transmitting elements (3) may be integrated in the catheter lumen or protrude to the catheter lumen (4)

FIG. 1d: The light producing or light transmitting element (3) may be provided as a major part of the catheter wall, or the catheter itself is made from light transmitting material FIG. 1e: The catheter lumen may be divided to functional units to allow independent or simultaneous applications of glue injection (5), blood aspiration, rinsing with fluids or gases, creation of negative pressure or injection of sclerosant media (5a), or for a guide wire.

Figure 2A:
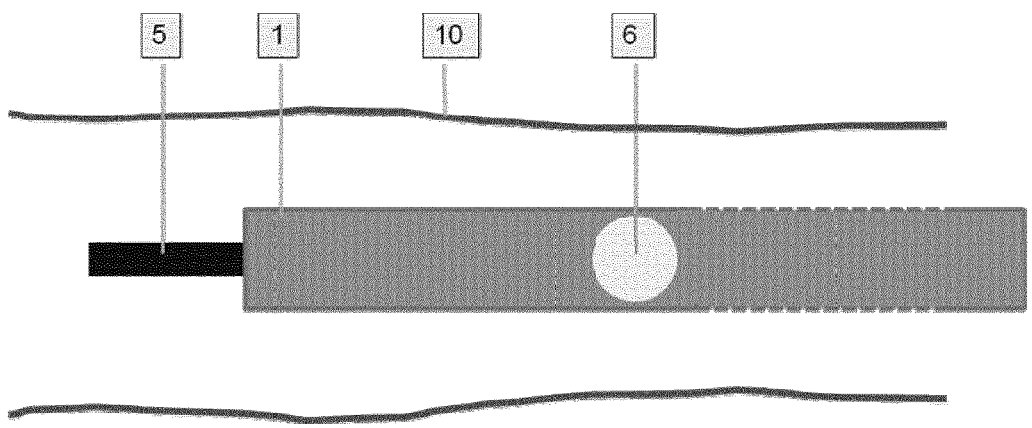

FIG. 2a: Application of light-activated glue in sclerotherapy in a vein (10) with a catheter system consisting of a main tube (1) with one or several optional side holes (6) and a separate smaller tube located within the main tube to transfer the glue. In this embodiment, the tube for glue transfer is relocatable. At the beginning of a treatment, the catheter system is introduced into the target vein.

FIG. 2b: Optionally, one or several of the tubes may contain sensors to monitor the placement of glue portions.

Figure 2C:
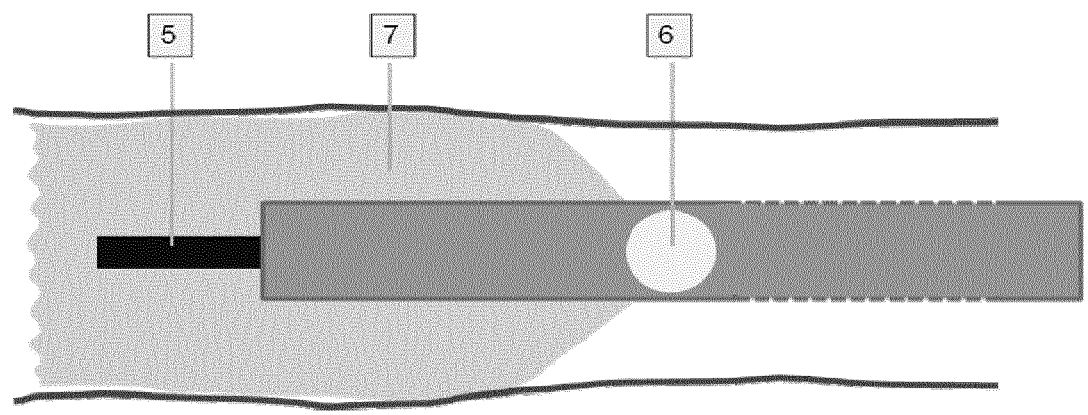

FIG. 2c: After positioning of the catheter in the target region, sclerosant medium (7) is deployed from the tip opening or from one or several side holes.

Figure 2D:
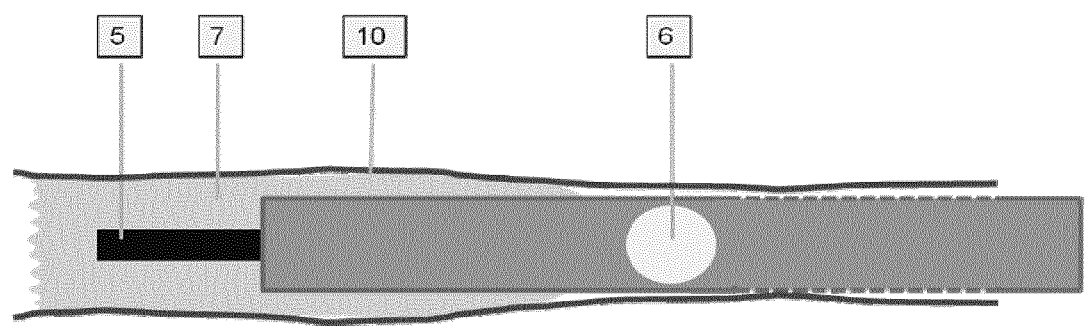

FIG. 2d: Due to the sclerosant medium the vein (10) will contract in a spasm and finally attach closely to the catheter. The vein collapse may be increased by negative pressure.

Figure 2E:
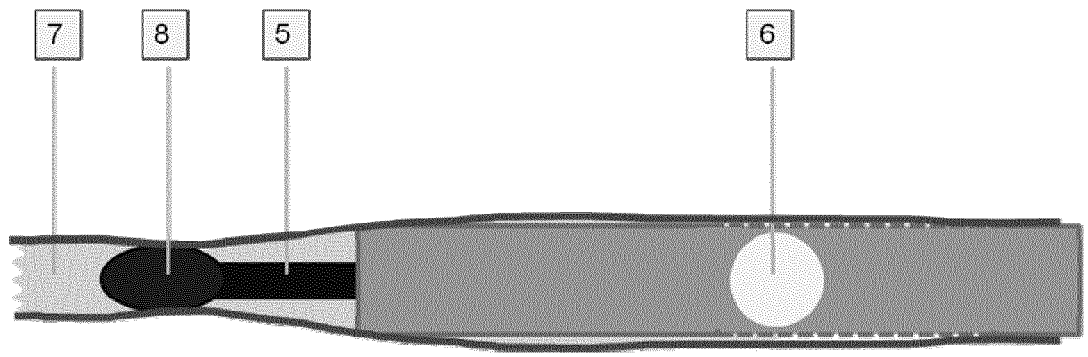

FIG. 2e: In the stage of spasm, glue (8) is deployed from the glue-transmitting tube (5).

Figure 2F:
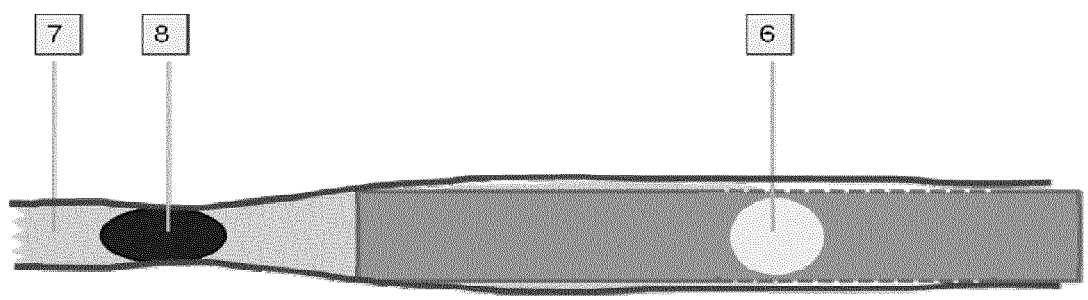

FIG. 2f: In this embodiment, the glue transmitting tube (5) is retracted to avoid glue bridging between the glue deposit (8) and catheter (1).

Figure 2G:
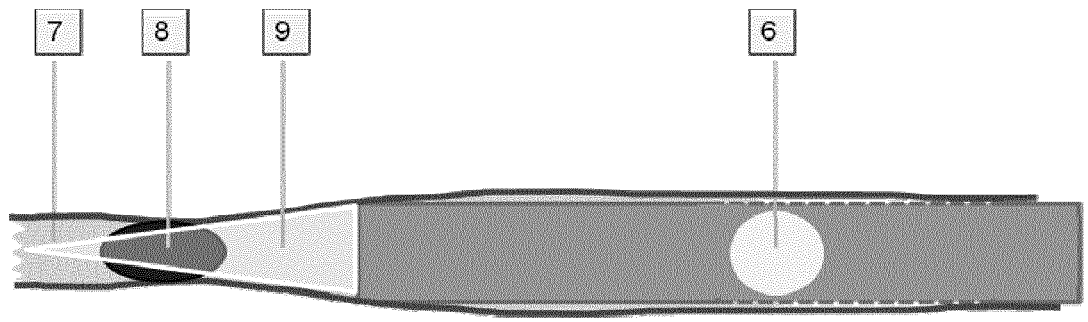

FIG. 2g: After separation of glue deposit and catheter the light for glue activation (9) is switched on for a time required to obtain an irreversible closure of the vein and tight adaption of the vein walls.

Figure 2H:
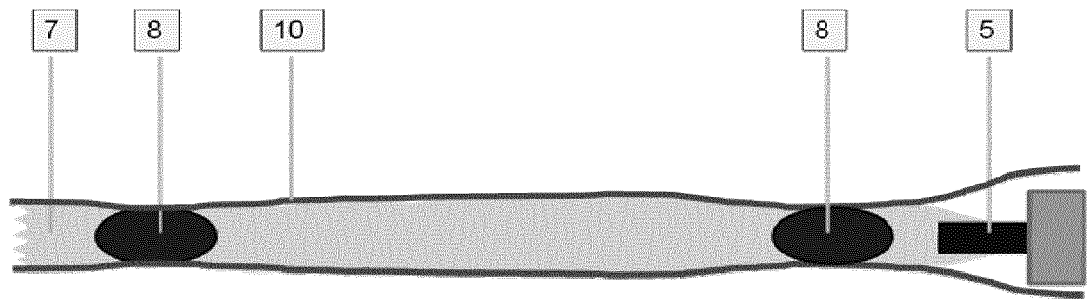

FIG. 2h: The procedure is continued by segmental sclerosing (7) and pointwise gluing (8) until the diseased vein (10) is completely treated.

Figure 2I:
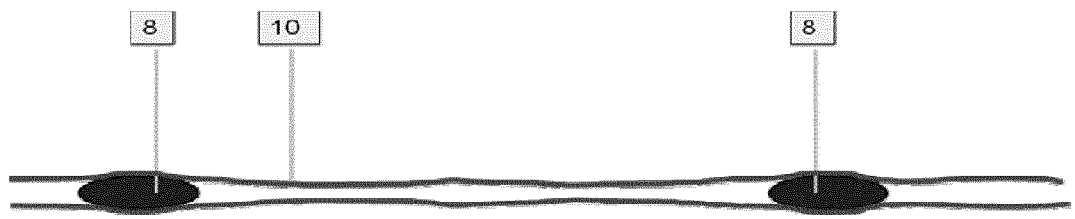

FIG. 2i: Treated vein after several weeks. It is shrunk due to the effects of sclerotherapy and pointwise light-activated gluing.

FIG. 3a: Another catheter embodiment uses a fixed glue conductor (5).

Figure 3B:
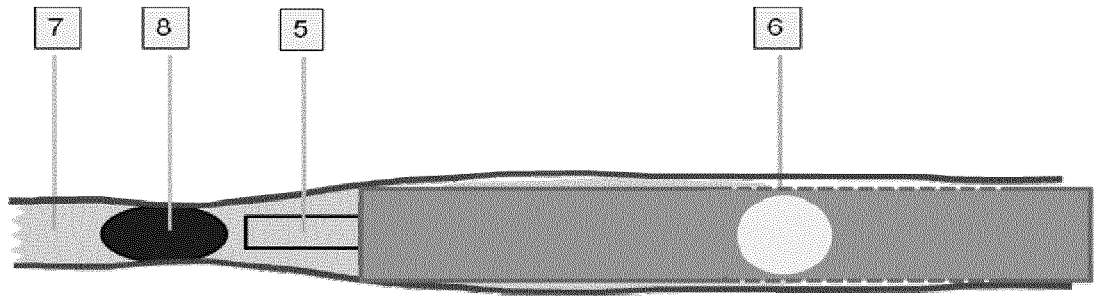

FIG. 3b: After applying sclerosant medium (7) and deploying a glue portion (8), the glue column within the glue conducting tube (5) is retracted to be out of reach of the glue activating light.

Figure 3C:
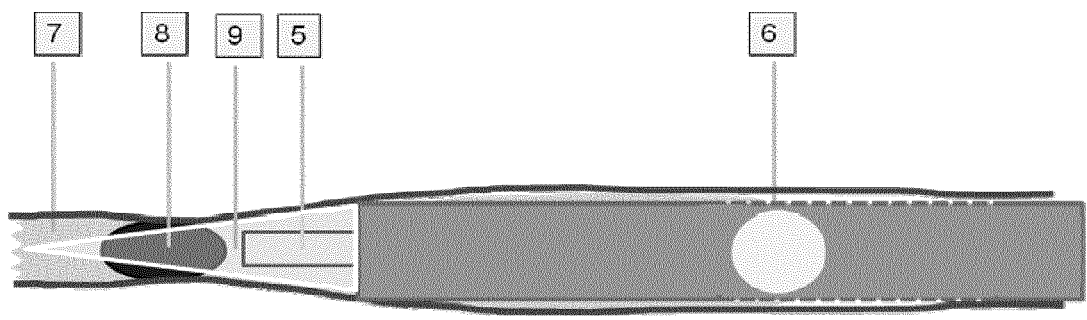

FIG. 3c: The glue portion is hardened by light activation (9).

Figure 4A:
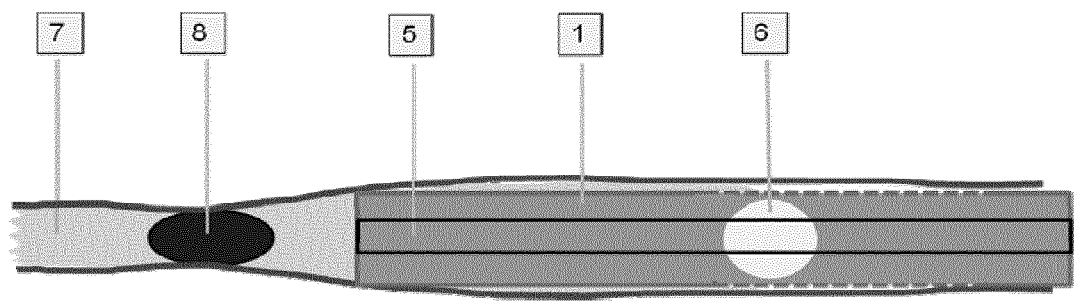

FIG. 4a: Another catheter embodiment uses a fixed glue conductor (5) not exceeding the main tube (1).

Figure 4B:
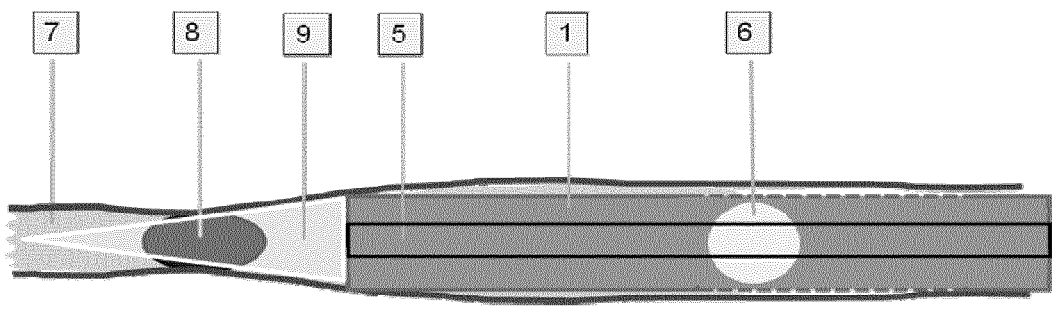

FIG. 4b: During light activation (9) no other glue is within reach of the light beam than the intended glue deposit.

The invention claimed is:

1. A double-tube injection and aspiration catheter device comprising an outer tube, a light source, a first container comprising light-hardening glue, and a second container comprising gas, wherein the light-hardening glue and the gas are applied in subsequent boli, wherein the light source is integrated in the catheter wall and/or within one lumen of the catheter,
   wherein the outer tube comprises a wall, at least one aperture and a tip,
   wherein at least one aperture being provided in the wall of the outer tube located at a distance of about between 5 mm and 40 mm from the tip, or several apertures positioned in a segment of 5-250 mm from the tip,
   wherein the outer tube comprises a decreased outer diameter resulting in a tapered outer tube,
   wherein a tip zone of the outer tube is modified such that a flow resistance occurs at the tip,
   wherein the double-tube injection and aspiration catheter is configured for independent or simultaneous applications of glue injection, blood aspiration, rinsing with fluids or gases, creation of negative pressure or injection of sclerosant media,
   wherein the double-tube injection and aspiration catheter further comprises a relocatable tube configured for glue deployment when advanced to a position 0.5-20 mm in front of the outer tube.

2. The double-tube injection and aspiration catheter device according to claim 1, wherein the light source is an optical fiber or another light-transmitting element.

3. The double-tube injection and aspiration catheter device according to claim 1, wherein the light source is able to generate, transmit and/or emit UV-light, visible light or infrared light, wherein UV-light is light with a wavelength of between 10 to 380 nm, visible light is light with a wavelength of between 381 to 780 nm and infrared light is light with a wavelength of between 781 nm to 1 mm.

4. The double-tube injection and aspiration catheter device according to claim 1, wherein the catheter has an inner diameter of 0.6 to 2.2 mm, an outer diameter of 0.8 to 2.8 mm and at least one lumen.

5. The double-tube injection and aspiration catheter device according to claim 1, additionally comprising a separation system.

6. The double-tube injection and aspiration catheter device according to claim 1 additionally comprising a sensor system.

7. A kit comprising a composition comprising a pharmaceutically acceptable tissue glue, and a sclerosant drug, in the form of a foam, wherein the glue is a pharmaceutically acceptable and biocompatible light-hardening glue, and a double tube injection and aspiration catheter device according to any of claims 1 to 3, 4, 5 and 6.

8. A method for sclerotherapy, the method comprising the steps of:
   a) preparing a target vessel;
   b) applying by means of a catheter device according to any of the claims 1 to 2, 3, 5 and 6 a tissue glue, wherein the glue is a pharmaceutically acceptable and biocompatible light-hardening glue;
   c) supplying a light source near to the adhesive; and
   d) activating light or energy in a way ensuring a separation of adhesive.

* * * * *